I

(12) United States Patent
Chow et al.

(10) Patent No.: US 6,827,831 B1
(45) Date of Patent: Dec. 7, 2004

(54) CONTROLLER/DETECTOR INTERFACES FOR MICROFLUIDIC SYSTEMS

(75) Inventors: Calvin Y. H. Chow, Portola Valley, CA (US); J. Wallace Parce, Palo Alto, CA (US); Richard J. McReynolds, San Jose, CA (US); Colin B. Kennedy, Mill Valley, CA (US); Luc J. Bousse, Los Altos, CA (US)

(73) Assignee: Callper Life Sciences, Inc., Mountain View, CA (US)

( * ) Notice: Subject to any disclaimer, the term of this patent is extended or adjusted under 35 U.S.C. 154(b) by 0 days.

(21) Appl. No.: 09/646,241

(22) PCT Filed: Aug. 26, 1998

(86) PCT No.: PCT/US98/17641

§ 371 (c)(1),
(2), (4) Date: Sep. 13, 2000

(87) PCT Pub. No.: WO99/10735

PCT Pub. Date: Mar. 4, 1999

Related U.S. Application Data

(63) Continuation-in-part of application No. 08/919,707, filed on Aug. 29, 1997, now Pat. No. 5,989,402.

(51) Int. Cl.[7] ...................... G01N 27/26; G01N 27/447; B01L 11/00
(52) U.S. Cl. ........................ 204/604; 204/450; 204/451; 204/453; 422/99; 422/100; 435/288.5; 436/180
(58) Field of Search ................................ 204/450, 451, 204/452, 453, 455, 600, 601, 602, 603, 604, 605; 422/100, 99; 436/180; 435/288.5, 288.6, 288.7

(56) References Cited

U.S. PATENT DOCUMENTS

| 4,390,403 A | 6/1983 | Batchelder |
| 4,908,112 A | 3/1990 | Pace |
| 5,126,022 A | 6/1992 | Soane et al. |

(List continued on next page.)

FOREIGN PATENT DOCUMENTS

| WO | WO 96/04547 | 2/1996 |
| WO | WO 97/02357 | 1/1997 |
| WO | WO 98/00231 | 1/1998 |

(List continued on next page.)

OTHER PUBLICATIONS

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798.

Jacobson, S.C. et al., "Fused Quartz Substrates for Microchip Electrophoresis," *Anal. Chem.* (1995) 67:2059–2063.

(List continued on next page.)

*Primary Examiner*—Nam Nguyen
*Assistant Examiner*—John S. Starsiak, Jr.
(74) *Attorney, Agent, or Firm*—Donald R. McKenna

(57) ABSTRACT

The present invention is generally directed to improved methods, structures and systems for interfacing microfluidic devices with ancillary systems that are used in conjunction with such devices. These systems typically include control and monitoring systems (620) for controlling the performance of the processes carried out within the device, e.g., monitoring and controlling environmental conditions and monitoring results of the processes performed, e.g., detection.

3 Claims, 11 Drawing Sheets

U.S. PATENT DOCUMENTS

| | | |
|---|---|---|
| 5,498,392 A | 3/1996 | Wilding et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,699,157 A | 12/1997 | Parce |
| 5,750,015 A | 5/1998 | Soane et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,942,443 A | 8/1999 | Parce et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |
| 6,042,710 A | 3/2000 | Dubrow |
| 6,046,056 A | 4/2000 | Parce et al. |
| 6,068,752 A | 5/2000 | Dubrow et al. |
| 6,071,478 A | 6/2000 | Chow |
| 6,074,725 A | 6/2000 | Kennedy |
| 6,080,295 A | 6/2000 | Parce et al. |
| 6,582,576 B1 * | 6/2003 | Chow et al. ............... 204/601 |

FOREIGN PATENT DOCUMENTS

| | | |
|---|---|---|
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |

OTHER PUBLICATIONS

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S. A., "High–throughput and ultra–high–throughput screening: solution—and cell–based approaches," *Current Opinions in Biotechnology* 2000, 11:47–53.

* cited by examiner

CONTROLLER/DETECTOR INTERFACES FOR MICROFLUIDIC SYSTEMS

CROSS-REFERENCE TO RELATED APPLICATIONS

This application is the National Stage of International Application No. PCT/US98/17641, which is a continuation-in-part of U.S. patent application Ser. No. 08/919,707, filed on Aug. 29, 1997, now U.S. Pat. No. 5,989,402, the full disclosure of which is incorporated herein by reference.

BACKGROUND OF THE INVENTION

Despite the advancements in the fields of microfluidics, microfabrication and the like, there remains a fundamental problem with the implementation of these technologies in achieving their full potential. Specifically, although microfluidic systems are readily applicable to high throughput, low volume, automatable chemical and biochemical analyses and syntheses, many of the advantages gained through the use of microfluidic systems are lost through the lack of interfacing systems that are capable of functioning at the horizons of these microfluidic systems. For example, one of the major advantages of these microfluidic systems is the ability to perform operations using extremely small fluid volumes, thereby requiring smaller amounts of potentially valuable reagents and/or samples. However, although a microfluidic system may be capable of operating with fluid volumes in the nanoliter range, the lack of fluid handling systems capable of delivering such volumes to these microfluidic systems renders this advantage substantially unrealized. Specifically, the user is still required to utilize reagents and/or samples in the 1 to 10 $\mu$l range.

One example of a fluidic interface which addresses these problems, namely, the introduction of samples and other fluids into microfluidic analytical systems, is described in commonly assigned U.S. application Ser. No. 08/671,986, filed Jun. 28, 1996, now U.S. Pat. No. 5,779,869 and incorporated herein by reference. In brief, the described system includes an electropipettor interfaced with the channels of a microfluidic device, for electrokinetically introducing very small volumes of samples or other materials into the microfluidic device.

In addition to fluidic interfaces, microfluidic systems also require additional device: world interfaces, including an interface between the device and the detection, sensing or monitoring means that are utilized with the system. Also required are interfaces between the device and the systems that control the operation of the device, such as systems that control fluid direction and transport within the device, and/or environmental conditions present within or around the device, and the like.

Microfluidic devices previously described in the literature have generally included only crude device: world interfaces which severely limited or eliminated a substantial proportion of the promised benefits of microfluidic systems, including automatability, ease of use, low volume and high throughput, which have been the goals of these systems.

Accordingly, there exists a need in the art for improved interfaces between microfluidic devices and the ancillary systems that are utilized with these microfluidic systems, such that these microfluidic systems can realize a greater proportion of their promised benefits. The present invention provides a solution to many of these and other problems.

SUMMARY OF THE INVENTION

The present invention generally provides improved methods, apparatuses and systems for interfacing microfluidic devices with the various systems used in conjunction with these devices, such as electrical control and monitoring systems, and the like. These improved interfaces provide microfluidic systems that are easier to use, e.g., "user friendly," are more readily automatable, and as a result, have higher throughputs than previously described analytical systems.

In a first aspect, the present invention provides an electrically controlled microfluidic system which includes a microfluidic device, an electrical controller and an electrical interface array. The microfluidic device generally comprises a body structure having an interior portion and at least a first exterior surface, a plurality of intersecting microscale channels disposed in the interior portion of the body structure, and a plurality of ports disposed in the body structure, communicating the exterior surface with the interior portion. Each of the ports is in fluid communication with at least one of the plurality of intersecting channels. The electrical control system comprises a plurality of electrical leads, each of the leads being operably coupled to a power source, where the electrical control system concomitantly delivers a voltage to each of the plurality of electrical leads. The electrical interface array permits the separate and removable coupling of each of the electrical leads with each of the plurality of ports, whereupon each of the leads is in electrical communication with a fluid disposed in each of the ports. The electrical interface array often includes a cover having at least a first surface, and a plurality of electrode pins mounted thereon, the electrode pins being oriented for insertion into the plurality of ports, each of the electrode pins being electrically coupled to a separate one of the electrical leads. Optionally, the electrical interface array further comprises a base adapted for receiving the microfluidic device, wherein an edge of the cover is attached to the base by a hinge, whereby the cover is capable of being rotatably closed over the microfluidic device mounted on the base, to insert the plurality of pins into the plurality of ports. In a further alternate aspect, the body of the device is planar in structure, and the electrical interface array comprises a plurality of electrical contact pads disposed along the at least one edge of the microfluidic device, each of the electrical contact pads being electrically coupled to at least one of the plurality of ports, and each of the plurality of electrical leads is positioned to contact a separate one of the plurality of contact pads. Alternatively, the electrical leads are disposed within a slot and oriented whereby each of the electrical leads contacts a separate one of the plurality of electrical contact pads, when the portion of the bottom layer extending beyond the top layer is inserted into the slot.

In a related embodiment, the present invention provides a "clam shell" comprising a base having at least one edge and at least an upper surface, the upper surface being adapted for receiving a microfluidic device. The clam shell also comprises a cover having at least a lower surface and at least one edge, the edge of the cover being connected to the edge of the base by a hinge, and the lower surface having at least a first electrical interface component. A microfluidic device is mounted on the upper surface of the base, the device comprising a body structure having an exterior surface, an interior portion defining a plurality of microscale channels, and a second electrical interface component disposed on the exterior surface and providing a plurality of separate electrical connections between the second electrical interface component and a plurality of separate points in the plurality of intersecting microscale channels, the second electrical interface component being complementary to the first electrical interface component and oriented to contact the first electrical interface component when the cover is closed over the microfluidic device. The first electrical interface array component optionally comprises an array of electrical contacts mounted on the lower surface of the cover and the second electrical interface array component comprises a plurality of electrical contact pads on the exterior surface of the microfluidic device, each electrical contact pad being in electrical communication with a separate point in the plurality of intersecting microscale channels.

In still another aspect, the present invention provides a base unit having a mounting surface adapted for receiving a microfluidic device, and a first electrical interface array component, the first electrical interface array component providing a plurality of electrical contacts, each of the electrical contacts being separately coupled to a different electrical lead from an electrical controller. Also included is a microfluidic device mounted on the mounting surface, the microfluidic device comprising a body structure having an exterior surface, an interior portion defining a plurality of microscale channels, and a second electrical interface component disposed on the exterior surface and providing a plurality of separate electrical connections between the second electrical interface component and a plurality of separate points in the plurality of intersecting microscale channels, the second electrical interface component being complementary to the first electrical interface component and oriented to contact the first electrical interface component when the microfluidic device is mounted on the mounting surface.

In an additional embodiment, the present invention provides a microfluidic system which comprises a microfluidic device having a body structure with at least first and second separate channel networks disposed therein. Each of the channel networks comprises a plurality of intersecting microscale channels, a first interface component on the body structure capable of delivering energy to the first channel network, and a second interface component on the body structure capable of delivering energy to the second channel network. The system also comprises a controller, having an energy source and a first surface adapted for mounting the body structure thereon in at least first and second fixed orientations, and including at least a third interface component operably coupled to the energy source, the third interface component being capable of transmitting energy from the energy source to the first interface component when the body structure is mounted on the mounting surface in the first orientation, and from the energy source to the second interface component when the body structure is mounted on the mounting surface in the second orientation.

In similar aspect, the present invention also provides a microfluidic system which comprises a microfluidic device having a body structure with at least first and second separate channel networks disposed therein. Each channel network comprises a plurality of intersecting microscale channels, a first interface component on the body structure capable of transmitting energy to or from the first channel network, and a second interface component on the body structure capable of transmitting energy to or from the second channel network. The system also comprises a detection system, which includes an energy detector and a first surface adapted for mounting the body structure thereon in at least first and second fixed orientations, and including at least a third interface component operably coupled to the energy detector, the third interface component being capable of transmitting energy to or from the first interface component to the detector when the body structure is mounted on the mounting surface in the first orientation, and to or from the second interface component, to the detector when the body structure is mounted on the mounting surface in the second orientation.

In yet another aspect, the present invention provides a microfluidic systems as described above, but incorporating electrical circuitry, an electrical conduit or electrode, which electrode comprises a thickness less than 1400 Å, and preferably between about 800 and 1400 Å. The electrode also typically comprises at least a first metal component selected from the group of tungsten, palladium, ruthenium, iridium, osmium and rhodium. In addition, the electrode does not substantially degrade at a metal/fluid interface under applied current densities greater than 0.5 mA/cm$^2$.

In another aspect, the present invention provides an interface for use with a microfluidic device. The microfluidic device has a plurality of intersecting microscale channels and a plurality of ports for receiving fluid. The interface comprises a base for receiving the microfluidic device. A structure is movable relative to the base between a first position and a second position. A plurality of electrical interface elements are affixed to the structure. The electrical interface elements are aligned so that each electrical interface element is electrically coupled to an associated port of the microfluidic device when the microfluidic device is received by the base and the structure is disposed in the first position.

Preferably, at least three electrical interface elements will be provided in the form of rigid electrodes. These electrodes can ideally extend from the structure into the fluid in the ports of the microfluidic device. The base of the structure may be coupled together using a hinge or other mechanical coupling arrangement, and the base will often fittingly receive the microfluidic device. This arrangement can be used to maintain alignment between a large number of very small ports of the microfluidic device and the electrodes of the interface, thereby allowing complex microfluidic devices to be easily removed and replaced.

In yet another aspect, the present invention provides a microfluidic device comprising a body structure having a port (for receiving fluid) and an interior portion. The interior portion defines a plurality of intersecting microscale channels. The interior portion blocks communication between the channels and the port. An electrical interface component electrically couples the fluid in the port to the channels, or to ports in fluid communication with the channels.

In yet another aspect, the invention provides a microfluidic device comprising a body structure including an upper layer and a bottom layer. The body structure has an interior portion defining first and second intersecting microscale channels. The first channel has an un-intersected terminus. The upper layer includes first and second ports therethrough. The first port is disposed at the terminus of the first channel. The interior portion blocks fluid communication between the first port and the second port. An electrically conductive film is disposed between the first and second layers. The film electrically couples a first fluid in the first port with a second fluid in the second port. These advantageous structures allow electrical potentials to be applied to a sample fluid by inserting an electrode into a fluidically isolated port containing saline or the like. The film (or other electrical conductor) need not be disposed between the layers. For example, alternative embodiments may include conductors overlaid over the upper layer (i.e., bridging between ports). Regardless, as compared to systems in which electrodes are directly inserted into each sample, the invention provides a reduced risk of cross-contamination when replacing one microfluidic device with another.

Preferably, electrodes of the interface structure will extend into ports containing an electrolyte. The electrolyte can be electrically coupled, in turn, to a sample fluid within a sample port using a thin film conductor deposited between the layers of the microfluidic body structure, typically using any of the thin film deposition techniques developed for production of integrated circuits, recording media or the like. The use of fluid to couple an electrode to the film enhances the reliability of the electrical connection and avoids damage to the film when the electrode is moved between a coupled position and a de-couple position.

In a still further aspect, the invention provides the use of an interface to connect a microfluidic device to an electrical controller. The interface has a structure that includes a plurality of fixed electrodes disposed thereon. The electrodes are operably coupled to the electrical controller. The fixed electrodes are positioned on the structure to be inserted into a plurality of ports on the microfluidic device when the structure is moved from a first position to a second position.

BRIEF DESCRIPTION OF THE DRAWINGS

FIG. 3 illustrates a further embodiment of an electrical interface between a microfluidic device and an electrical controller. FIG. 3A illustrate the interface components present on a microfluidic device from a top view, while

FIG. 4A shows an alternate structure of a microfluidic device, while FIGS. 4B–4D illustrate the device with an optional coupler assembly from various perspectives.

DESCRIPTION OF THE PREFERRED EMBODIMENT

Figure 1:
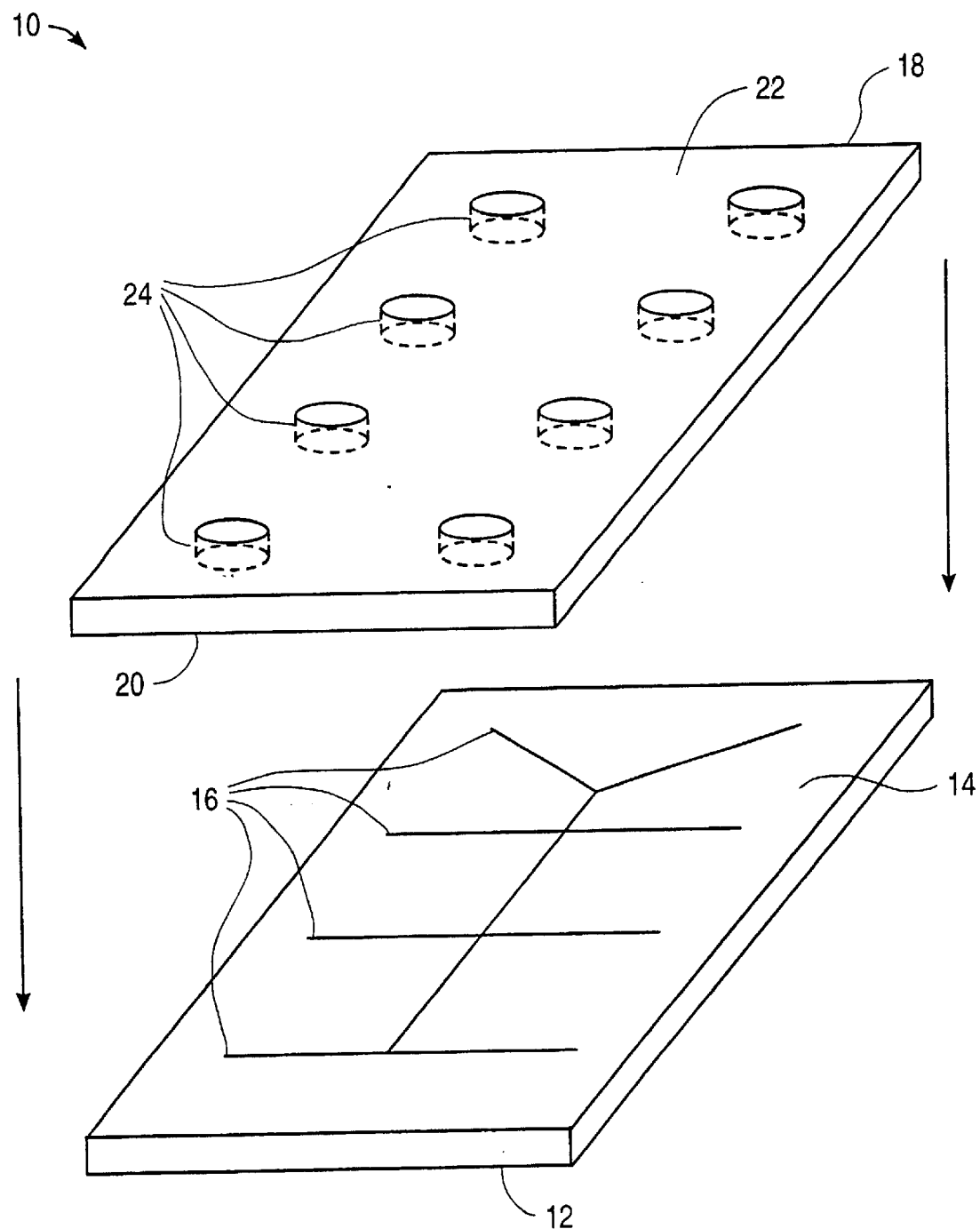
FIG. 1 schematically illustrates one embodiment of a microfluidic device fabricated from a plurality of laminated or bonded parts, for use in accordance with the methods and systems of the present invention.

The present invention is generally directed to improved methods, structures and systems for interfacing microfluidic devices with ancillary systems that are used in conjunction with such devices. These systems typically include fluid handling systems for delivering fluids to a microfluidic device, e.g., sampling systems, control and monitoring systems for monitoring the processes carried out by the microfluidic devices and for controlling the performance of those processes, e.g., controlling internal fluid transport and direction, monitoring and controlling environmental conditions and monitoring results of the processes performed, e.g., detection.

In a first general aspect, the present invention provides electrically controlled microfluidic systems which have improved interfaces between the device itself and the electrical controlling system. Such systems include a microfluidic device made up of a body structure which includes an interior portion and an exterior portion. The devices include a plurality of intersecting channels disposed within, and typically defined by, the interior portion of the body structure. Typically, such microfluidic devices also include a plurality of ports disposed in the body structure, communicating the exterior portion of the device with the interior portion of the device, where the ports are in fluid communication with one or more of the plurality of intersecting microscale channels.

As used herein, the term "microscale" or "microfabricated" generally refers to structural elements or features of a device which have at least one fabricated dimension in the range of from about 0.1 $\mu$m to about 500 $\mu$m. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 1 $\mu$m and 100 $\mu$m, and often between about 1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross or "four-way" intersections, "T" intersections, or any number of other structures whereby at least two channels are in fluid communication.

The body structure of the microfluidic devices described herein is typically fabricated from a number of discrete elements which, when assembled, form or define the integrated microscale channels and chambers of the microfluidic devices. Typically, the body structure comprises an aggregation of two or more separate layers which when appropriately mated or joined together, form the body structure of the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates a two-layer body structure for the microfluidic device 10. In preferred aspects, the bottom portion of the device 12 comprises a solid substrate that is substantially planar in structure, and which has at least one substantially feat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/919,707, filed Apr. 14, 1997, now U.S. Pat. No. 5,989,402 and which is incorporated herein by reference in its entirety for all purposes.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, and as noted above, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

These devices may be used in a variety of applications, including, e.g., the performance of high throughput screening assays in drug discovery, immunoassays and genetic analysis for research and diagnostic applications, and the like. As such, the devices described herein, often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. patent application Ser. Nos. 08/761,575, now U.S. Pat. No. 6,046,056 and 08/760,446, now U.S. Pat. No. 5,880,071 each of which was filed on Dec. 6, 1996, and is hereby incorporated by reference in its entirety for all purposes.

In preferred aspects, the electrically controlled microfluidic devices, methods and systems described herein, employ electrokinetic material transport systems, and preferably, controlled electrokinetic material transport systems. As such, the microfluidic systems of the present invention typically include an electrical control system, for controlling and/or monitoring the processes being carried out by the microfluidic device. In at least one aspect, the electrical control system includes a plurality of electrical leads, each of the leads being operably coupled to a power source, whereby the electrical control system is capable of concomitantly delivering voltages to each of the plurality of electrical leads. Examples of preferred power sources are described in e.g., U.S. patent application Ser. No. 08/678,436, filed Jul. 3, 1996 now U.S. Pat. No 5,800,690, and incorporated herein by reference.

The systems of the present invention also include an electrical interface array, permitting each of the electrical leads to be separately, and preferably, removably coupled to each of the plurality of ports on the microfluidic device, whereupon each of the leads is placed in electrical communication with a fluid that is disposed in each of the ports.

As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of cations at near the fluid/surface interface, or a positively charged sheath surrounding the bulk fluid in the channel. Application of a voltage gradient across the length of the channel, will cause the positively charged sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and generally encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least two intersecting channels having at least three unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, while applying no voltage to the top and bottom termini of the vertical channel. However, this type of material flow through the intersection results in a substantial amount of diffusion at the intersection, resulting from the natural diffusive properties of the material being transported in the medium used, at the intersection.

In controlled electrokinetic material transport, the material being transported across the intersection is constrained by low level current from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of current is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient between the left and top termini. A constraining flow is directed from the bottom arm to the top arm by applying a similar voltage gradient along this path (between the bottom terminus and the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed into the right arm of the horizontal channel, in this manner.

Although described for the purposes of illustration with respect to a four-way or cross intersection, these controlled electrokinetic material transport systems can be readily adapted for more complex interconnected channel networks, e.g., arrays of interconnected parallel channels. Similarly, although electrodes are generally placed into electrical contact with the termini of the various channels in the system, electrodes may also be placed in electrical contact with intermediate points in the channels, depending upon the nature of the operation being performed.

In the simplest embodiment, the electrical interface array which provides at least one component of the overall electrical interface or connection between the electrical controller and the plurality of ports on the microfluidic device, comprises a series of electrode pins, each of which is appropriately positioned for insertion into each of the plurality of ports on the device. In at least one embodiment, such electrodes are fixedly mounted on the surface of a planar cover element. The cover element is then placed over the surface of the device which includes the ports disposed therein, e.g., the top substrate, whereupon the electrodes are inserted into the ports. In preferred aspects, the cover element is provided as the cover of a hinged chamber, well, cavity or recessed region into which the microfluidic device is inserted. The cover element, or a housing in which the cover element is mounted, is preferably connected to the edge of the chamber via a hinge along one edge of the cover element, such that the cover element may simply be rotated on the hinge into the closed position, whereupon the electrodes are placed into the ports. This "clam-shell" structure permits simple and rapid interfacing of microfluidic devices with electrical control systems. The clam-shell also helps to secure the microfluidic device against additional elements of the overall system, e.g., heating blocks, heat sinks, optical systems, etc., to ensure the most efficient interfacing of the device with these components. Additionally, the cover element, or the entire clam-shell portion of the system is readily interchangeable with different covers having different electrode pin configurations, permitting adaptation to devices which have alternate port configurations. Examples of such interchangeable systems are described in commonly assigned U.S. patent application Ser. No. 08/691,632 filed Aug. 2, 1996, now U.S. Pat. No. 6,390,023 which is hereby incorporated herein by reference in its entirety for all purposes.

Figure 2A:
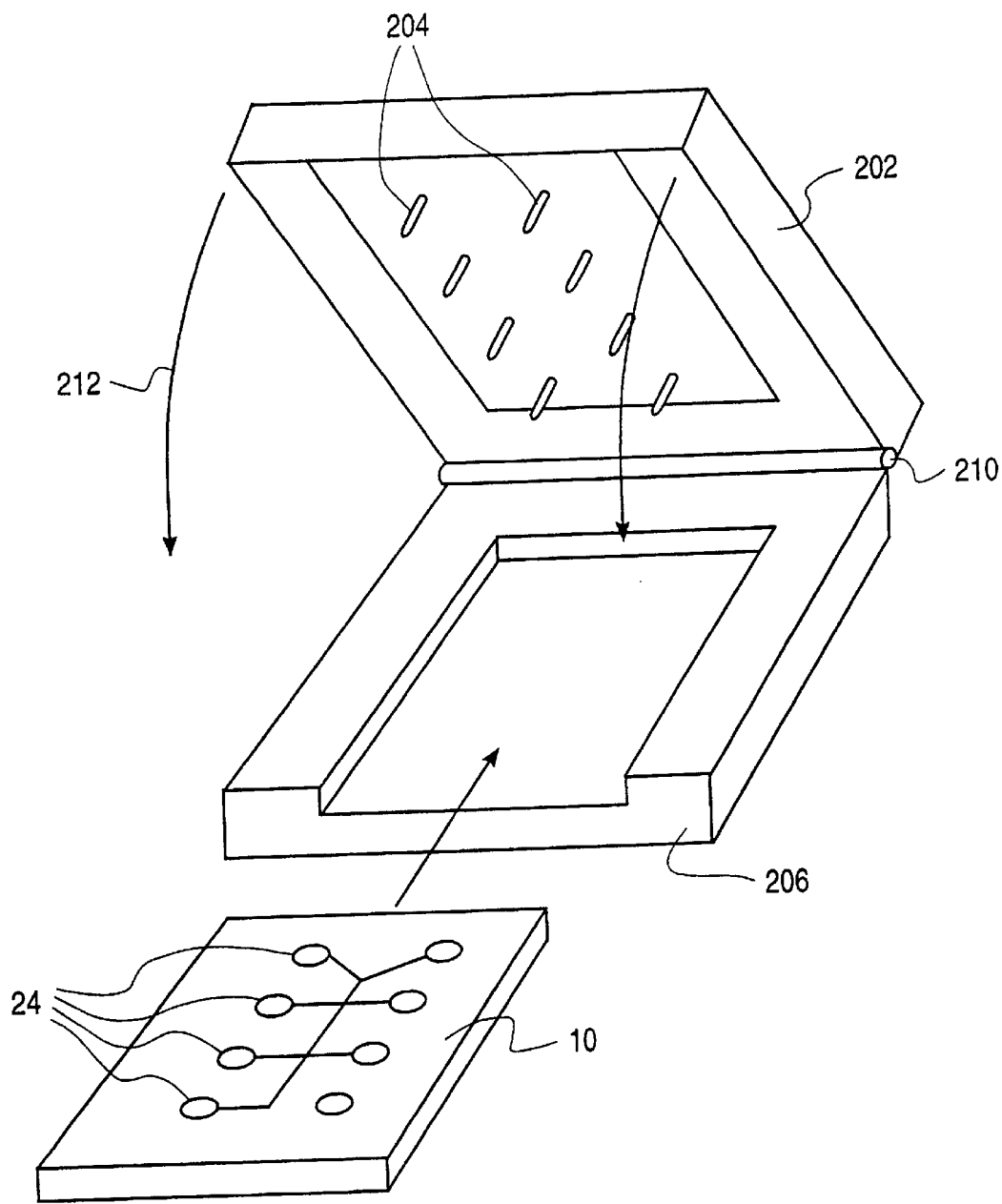
FIG. 2A illustrates one embodiment of an improved electrical interface between a microfluidic decie and electrical controller.

FIG. 2A provides an illustration of cover element 202, which has a plurality of electrode pins 204 disposed thereon. The pins are oriented on the surface of the cover element such that they will communicate with the ports 24 of the microfluidic device 10, when the cover element is placed over the top surface of the device. Each of electrode pins 204 is electrically coupled to one of the electrical leads from the electrical controller (not shown). Typically, this connection is via electrical circuitry from each separate pin, extending through the rear portion of the cover element 202 to connect to each separate electrical lead on the controller, however, in some cases, multiple electrodes may be coupled to the same electrical lead, e.g., where two electrodes are intended to provide the same voltage level at two different ports of the device. Alternatively, the circuitry from each electrode pin is connected to one port of a multi-port connector, e.g., at the rear portion of the cover, to which is coupled a complementary multi-port connector from the controller, which connector includes electrical connections to the various electrical leads from the controller. These multi-port connectors are generally commercially available, and are readily connected to the various electrical leads on the controllers and the electrodes present in the cover. As shown, the cover element 202 is connected to a separate structural element or base 206, which includes a nesting well, cavity or recessed region 208 disposed therein. The cover 202 is connected to the base 208 via hinge 210. The microfluidic device 10 is inserted into the nesting well 208. Arrows 212 illustrate the direction of rotation of the cover element 202. After inserting a microfluidic device into the nesting well 208, the hinged cover element is rotated down on the hinge 210 until the electrode pins 204 are in contact with fluid that is contained within the ports 24 of the device, and in fluid communication with the channels and/or chambers of the device. The use of this type of interface permits the user to simply insert the microfluidic device 10 into the nesting well and close the cover, whereupon the device is interfaced with the electrical controller. It will be readily appreciated that microfluidic devices of varied sizes, shapes and configurations may be inserted into a given interface (e.g., base and cover) through the incorporation of the device into a uniformly sized adapter plate. The use of such adapter plates for interfacing differently sized or differently configured microfluidic devices with a particular controller element is described in greater detail in U.S. patent application Ser. No. 08/691,632 filed Aug. 2, 1996, now U.S. Pat. No. 6,390,023 previously incorporated herein by reference.

As shown in FIG. 2A, the electrode pins 24 are oriented in a grid format, e.g., in columns and rows. Although a single column or row of electrodes may be provided in accordance with the present invention, e.g., as described in greater detail herein, typically, such gridded arrays of electrodes will be at least two rows and at least two columns of electrodes, i.e., 2×2. In preferred aspects, the gridded array of electrodes will comprise at least two columns of electrodes and at least three rows of electrodes. In many embodiments, the gridded array may include at least four columns and at least four rows of electrodes (e.g., a 4×4 gridded array). Although it is not required, in order to promote uniformity, the spacing between the rows and columns of the electrode array is preferably equal, e.g., each probe is equidistant from the adjacent probes in the same column and row. By arranging the electrode pins as a gridded array of electrodes, one is able to standardize the electrode format, and provide microfluidic systems having a matching, e.g., complementary, port format. In particular, because one can create a wide variety of channel geometries for performing a given fluidic operation within a microfluidic device, the operations performed within the interior portion of a microfluidic device, e.g., within the channels and chambers, often have little influence on the orientation of the ports on the surface of the device, and consequently, the electrodes for interfacing with those ports. As such, orientation of the electrodes, and complementary ports in a gridded format permits the utilization of a standard electrode/device interface, regardless of the operation for which the device will be used.

Where fluids are contained within relatively small areas, e.g., in the reservoirs of the devices of the present invention, such systems can often produce a certain amount of water vapor, which vapor is particularly localized at or near the ports of the microfluidic device. This vapor generation is increased where temperatures of the fluids are elevated, e.g., when applying substantial electrical currents through these fluids. Condensation of these vapors as liquid, e.g., on the surface of the microfluidic device and/or the surface of the cover element, can result in an electrical connection being made between two or more neighboring or adjacent electrode pins, across the surface of the device or the cover element, e.g., a shorting out of the electrodes. As such, it is generally desirable to either prevent this condensation, or, in the event of such condensation, prevent the formation of the electrical connection between adjacent electrodes across the external surfaces of the device. As such, in preferred aspects, the microfluidic systems are provided with a barrier between adjacent electrodes when they are inserted into the ports of the device. Preferably, the barrier forms a liquid tight seal between adjacent ports and/or electrodes. These barriers may be fabricated or placed onto the surface of the cover element, or alternatively, on the surface of the microfluidic device, e.g., as a gasket.

Figure 2B:
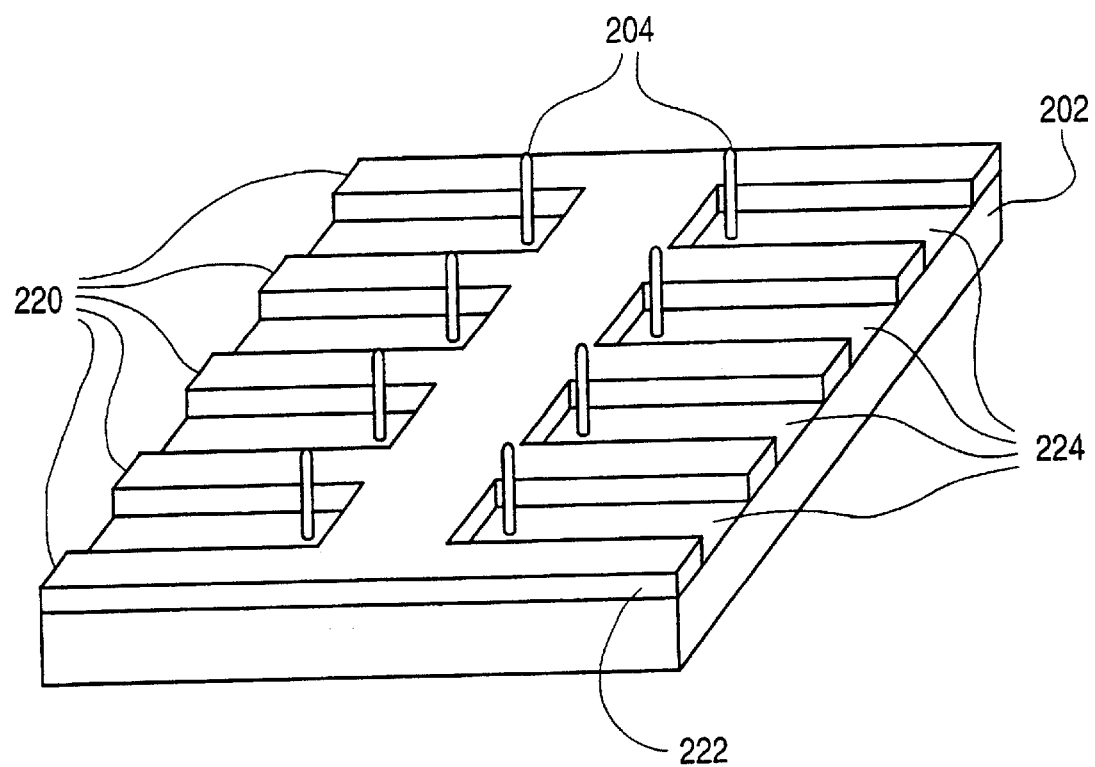
FIG. 2B illustrates an alternate configuration for the cover element of the interface shown in FIG. 2A.

One example of such a liquid tight barrier structure is shown in FIG. 2B, which illustrates an alternative embodiment of the cover element 202. As shown, the barrier is a part of the cover element 202. In particular, raised regions 220 are provided on the surface of the cover element 202, between the various electrode pins 204 that are disposed thereon. The raised regions are of such height as to permit insertion of each of the electrode pins into its respective port of a microfluidic device and contact the fluid therein, while the raised regions securely contact the surface of the microfluidic device, providing a fluid tight seal between the ports/electrodes of the system. The raised regions 220 are optionally provided as a separate part 222, e.g., as shown, which is mated, bonded or otherwise attached to the surface of the cover element 202, or are fabricated into the surface of the cover element 202. In preferred aspects, these raised regions, or the cover element as a whole, are either fabricated from or coated with a hydrophobic material, e.g., a polymer such as polytetrafluoroethylene (TEFLON™), to provide additional fluid sealing capabilities when these regions are contacted with the top surface of the microfluidic device. In alternative aspects, the barrier may be provided in whole or in part, on the surface of the microfluidic device which includes the ports. For example, a hydrophobic coating is optionally provided on the top surface of the device, or alternatively, gasket-like structures are provided upon the surface of the device, e.g., fabricated upon or mated with that surface. When the cover element 202 is placed over the surface of the device to interface the electrical controller with the ports of the device, these gasket-like structures provide a fluid tight barrier between the neighboring or adjacent ports/electrodes. Again, the height of these structures is such that the electrodes are in electrical contact with the fluids disposed in the ports, when the cover element is placed over the device. Typically, such electrodes will range in length of from about 1 mm to about 10, from their tips to the point at which they are attached to the cover element. The electrodes may be fixedly mounted in the cover, or alternatively, may be spring mounted, to maintain the electrode in optimal communication with the port, or fluids therein, and to prevent damage to the electrodes or the microfluidic devices upon closing the cover. Although the barrier is generally described as including raised regions, it will be readily apparent that the cover element may be provided with recessed regions 224 surrounding each of the various electrode pins. Recessed regions 224 are generally provided extending from around the electrodes to the near edge of the cover. In addition to presenting a potential fluid barrier between adjacent electrodes, the recessed region provides an air passage or vent from each port to the surrounding environment, permitting escape of fluid vapors, gases and the like, which can adversely effect the operation of the system, either through condensation, pressure effects or otherwise.

In optional embodiments, the electrical interface array comprises a plurality of electrical contact pads that are electrically coupled to each of the various ports of the microfluidic device. These electrical contact pads are generally disposed along at least one edge of the microfluidic device. These electrical contact pads typically comprise a small electrically conductive surface which is contacted by the electrical leads of the electrical controller. In such cases, the electrical lead will generally include a mechanism for maintaining the electrical lead in contact with the contact pads, when the leads are placed in contact with the electrical interface array, e.g., a pressure contact or wiping contact. Such mechanisms are typically included within commercially available electrical connectors, which are readily adaptable for use with the electrical leads of the controller. Each of the electrical leads is then positioned, e.g., within the coupler, to contact a separate one of the electrical contact pads on the device.

Figure 3A:
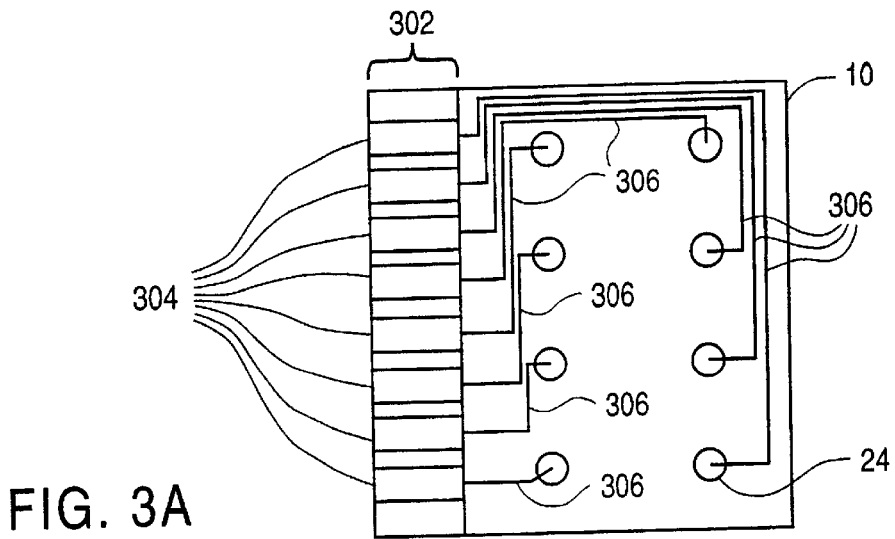
Figure 3B:
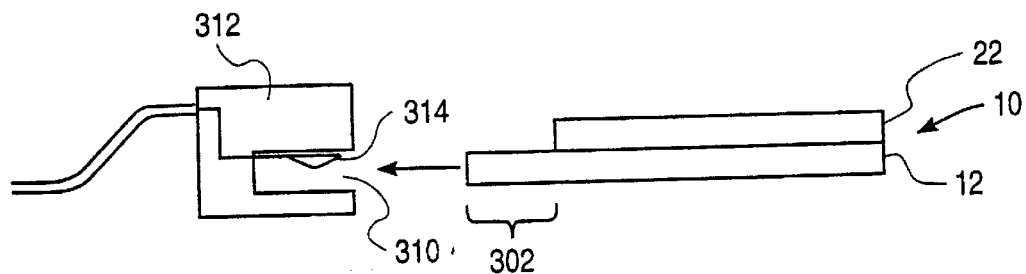
FIGS. 3B and 3C illustrate the device from the side and perspective views, in combination with a complementary interface element from an electrical controller.

An example of a microfluidic device incorporating this type of electrical interface array is illustrated in FIG. 3. This figure illustrates the device from a top view (3A), end view (3B) and perspective view (3C). As shown, the device 10 is fabricated in a layered format from at least two separate planar elements, a top substrate 22 and a bottom substrate 12 (FIG. 3B). The bottom substrate 12 has an extended portion 302, which extends beyond the top substrate along at least one edge. A plurality of electrical contact pads 304 are provided upon this extended portion 302. Typically, these contact pads 304 are fabricated from an appropriately conductive material and are deposited upon the exposed surface of the extended portion of the lower substrate using well known deposition methods, e.g., chemical vapor deposition, sputtering, thermal or E beam evaporation, electroplating, and the like. The individual traces and pads are then defined with a photolithographic lift-off technique. Each of the electrical contact pads is electrically coupled, via wires or circuitry 306, to a separate one of the various ports 24 that are disposed through the top substrate of the device 10. Typically, this circuitry 306 is deposited upon the upper surface 14 of the bottom substrate 12 prior to the bonding of the bottom substrate 12 to the top substrate 22. In this situation, it will be appreciated that the circuitry 306 is sufficiently thin as to permit complete bonding of the two substrate layers, i.e., to prevent leakage of fluidic elements within the interior portion of the device. Sufficiently thin circuitry is generally less than about 1500 Å thick, preferably between about 500 and 1400 Å thick, and is generally deposited upon the upper surface of the bottom substrate using any of the above described methods.

In preferred aspects, the circuitry 306 is comprised of sufficiently durable material to prevent its degradation, particularly at the metal/fluid interface, e.g., the point at which the electrode contacts the fluid contained within the ports or channels of the microfluidic device, under the elevated voltages and currents applied across that circuitry, as well as the elevated temperatures that may be involved in the process of bonding substrates together. In particular, the thin circuitry utilized in the devices described herein will often be subjected to relatively high currents and voltages which are typically passed through to fluid containing channels. Further, in the case of devices fabricated from thermally bonded substrate layers, this fabrication can include bonding temperatures in the range of 500 to 1400° C., and typically from about 500 to about 800° C. In particular, some metals that are commonly utilized in the patterning of electrical circuitry on solid substrates, such as pure chrome and pure titanium, are subject to substantial oxidation under conditions of thermal bonding, e.g., using the temperatures described above.

By way of example, electrodes comprising a gold conductive layer on a chrome adhesion layer, patterned on a glass substrate, showed substantial degradation following the thermal bonding process (extensive discoloration, indicative of substantial oxidation), and were unable to withstand application of normal operating currents. Similarly, electrodes comprised of a gold conductive layer on a titanium adhesion layer were capable of withstanding the thermal bonding process, but peeled and disappeared under the normal operating current densities of approximately 50 mA/cm$^2$.

Accordingly, in preferred aspects, the devices of the present invention include circuitry that has a thickness less than 1500 Å, and preferably, between about 800 and about 1400 Å, but which circuitry is capable of withstanding normal current ranges applied through the circuitry without substantially degrading, i.e., greater than 1 $\mu$A, preferably in the range of 10 to about 1000 $\mu$A. In the case of the devices of the present invention, this circuitry is thus capable of withstanding current densities greater than 10 $\mu$A/cm$^2$, preferably greater than 0.1 mA/cm$^2$, more preferably greater than 0.5 mA/cm$^2$, and still more preferably, greater than 1 mA/cm$^2$. In some applications, the circuitry is capable of withstanding greater than 5 mA/cm$^2$, more preferably, greater than 10 mA/cm$^2$, often greater than 50 mA/cm$^2$, and in certain instances, greater than 100 mA/cm$^2$, without being substantially degraded at the metal/fluid interface. Further, the circuitry described herein is also typically capable of withstanding bonding temperatures greater than 500° C., and preferably between about 500 and 1400° C., without being substantially degraded during the thermal bonding process.

An electrode that is not "substantially degraded" as that phrase is used herein, refers to an electrode that has lost less than 20% of either its thickness (as measured by profilometry), or its current carrying capacity (as measured by change in impedance). Preferably, such electrodes will lose less than 10% and more preferably, less than 5% of their thickness or current carrying capacity.

Generally, the circuitry will include a conductive layer that includes one of the metals selected from tungsten, palladium, ruthenium, iridium, osmium or rhodium. In preferred aspects, the conductive layer comprises tungsten as at least one element of the conductive layer (also referred to herein as an electrode, electrical circuitry or electrical conduit). The tungsten containing portion of the electrical circuitry may be provided as the adhesion layer or as the entire electrical layer. By "tungsten containing" is meant a metal layer that may be entirely tungsten or a tungsten alloy or amalgam. In preferred aspects, the tungsten containing layer is titanium/tungsten alloy. This alloy is typically primarily, e.g., greater than 50% tungsten, preferably, greater than 70% tungsten, and more preferably, greater than 80% tungsten.

In particularly preferred aspects, the electrical circuitry includes a titanium/tungsten adhesion layer with a platinum overlay (Pt/TiW), where the adhesion layer is in the range of approximately 50 to 600 Å thick, preferably about from about 300 to 500 Å thick, while the platinum layer is in the range of approximately 400 to 1200 Å thick, preferably from about 700 to about 1100 Å thick. Electrical circuitry comprised of this material, and which falls within the preferred thickness ranges, has demonstrated an ability to withstand both the high temperatures of the bonding process as well as the high current densities applied in the microfluidic systems described herein. More conventional electrical circuitry compositions, e.g., gold/chrome (Au/Cr), platinum/chrome (Pt/Cr), and the like, showed substantial degradation under these conditions, and particularly at the fluid/metal interface.

Figure 3C:
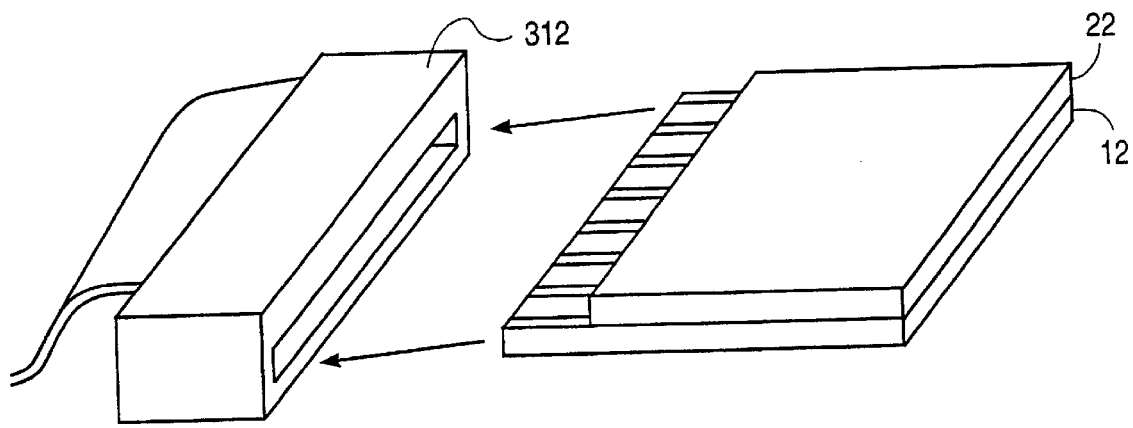

FIGS. 3B and 3C illustrate the interfacing of the microfluidic device shown in FIG. 3A, with the electrical leads from the electrical controller. As shown, the microfluidic device 10 may be readily inserted into an appropriately sized slot 310 on a multi-port coupler 312. Within the slot 310, is a series of electrical contacts 314 or leads, which are electrically coupled to the electrical controller (not shown). Each contact is positioned within the slot 310 to separately contact each of the electrical contact pads 304 on the device 10. Each of these contacts is typically a flexible contact 314, e.g., flexibly mounted within the slot 310, whereby when the extended region 302 of the device 10 is inserted into the slot 310, each of the electrical contacts in the slot is pressed against its corresponding electrical contact pad 304 on the device 10.

In a related embodiment, the electrical interface array is optionally disposed along more than one edge of the microfluidic device. This is accomplished in a similar manner as provided in FIG. 3, except that the bottom substrate extends beyond more than one edge of the top substrate, providing extended regions along several or all edges of the microfluidic device. In one preferred aspect, the extended portion of the bottom substrate is provided by the presence of recessed regions of the top substrate, exposing portions of the surface of the bottom substrate upon which electrical contact pads are disposed. An example of a device incorporating this alternative structure for an electrical interface array is illustrated in FIGS. 4A–4D.

As shown, in FIG. 4A, the device 10 is again fabricated with a layered construction, including a top substrate 22 and a bottom substrate 12, where the top substrate includes a plurality of ports 24 disposed therethrough, providing access to the channels/chambers in the interior portion of the device (not shown). A plurality of recessed regions 402 are provided along the edges of the top substrate 22. When the top substrate is mated with the bottom substrate, these recessed regions in the top substrate leave portions or regions 404 of the surface of the bottom substrate exposed. The electrical contact pads, as previously described, are deposited in these exposed regions, providing access points for connection to the electrical leads from the electrical controller. Again, these contact pads, are electrically coupled to the various ports 24 of the device 10, e.g., via appropriate circuitry.

Figure 4A:
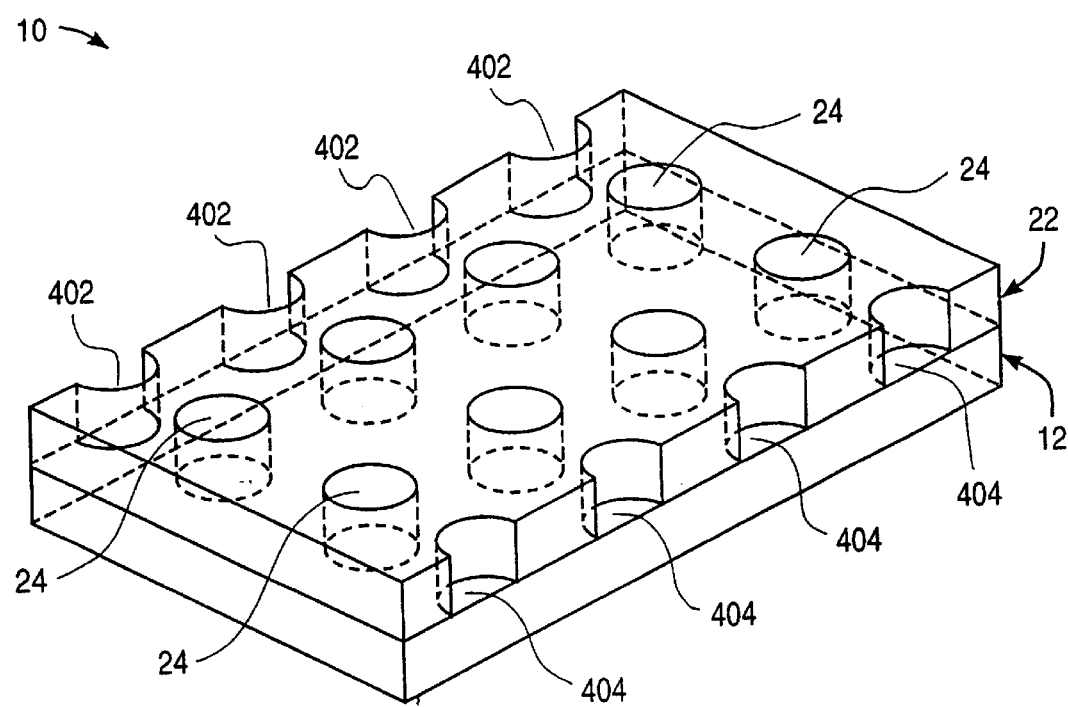
FIGS. 4A–4D illustrate an alternate embodiment of a microfluidic device incorporating an electrical interface array.

In the case of the device shown in FIG. 4A, interfacing the device with the electrical controller is optionally carried out by any one of the methods described above. For example, a cover element, e.g., a clam-shell as shown in FIG. 2, is used to interface the device with the controller. In this instance, the electrode pins, or optionally, corresponding, flexible electrical contacts, mounted on the cover element, are positioned to contact and are preferably contacted with or pressed against the electrical contact pads in the recessed regions of the top substrate of the device, e.g., through the inclusion of a pressure or wiping contact.

Figure 4B:
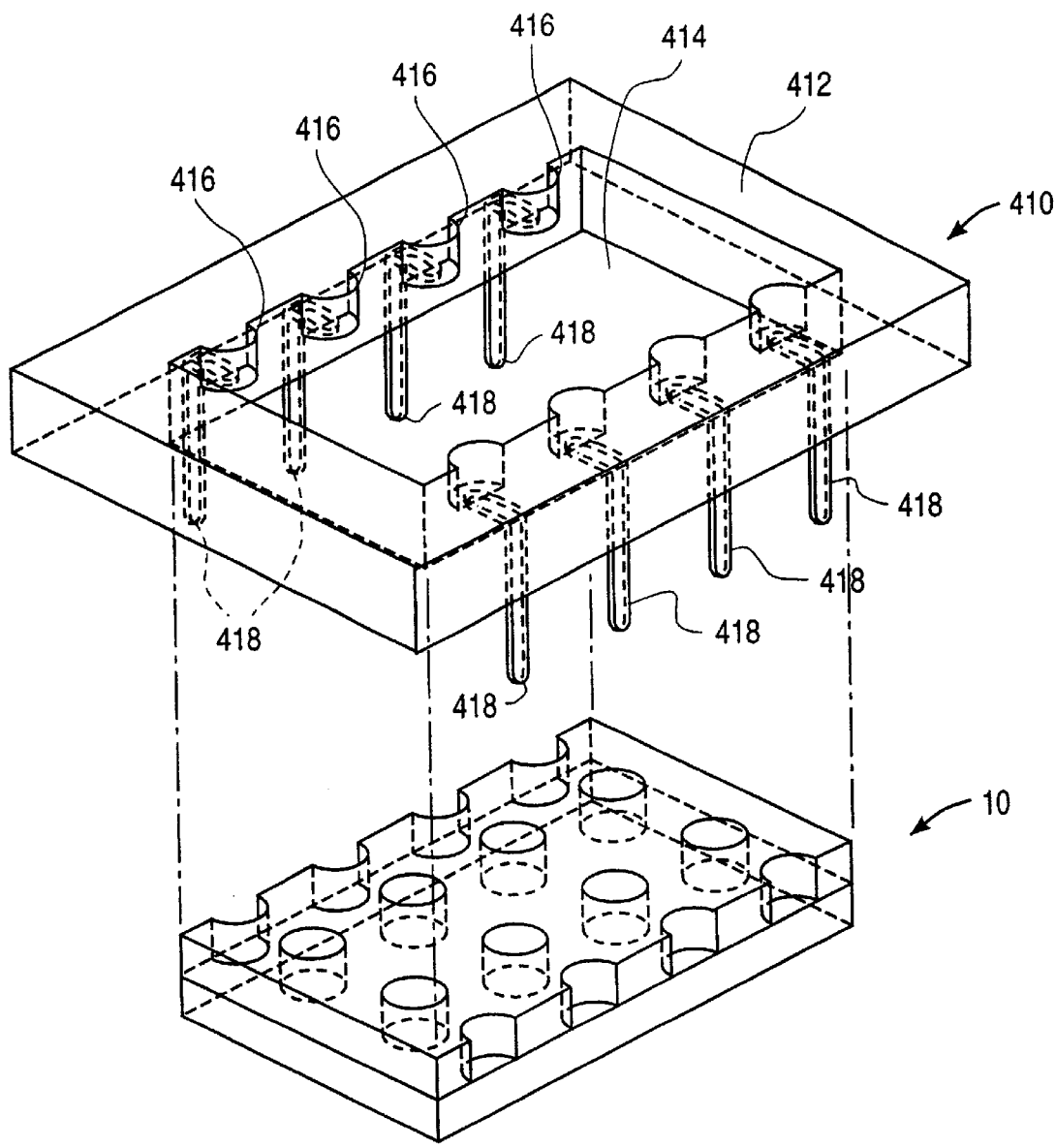
Figure 4C:
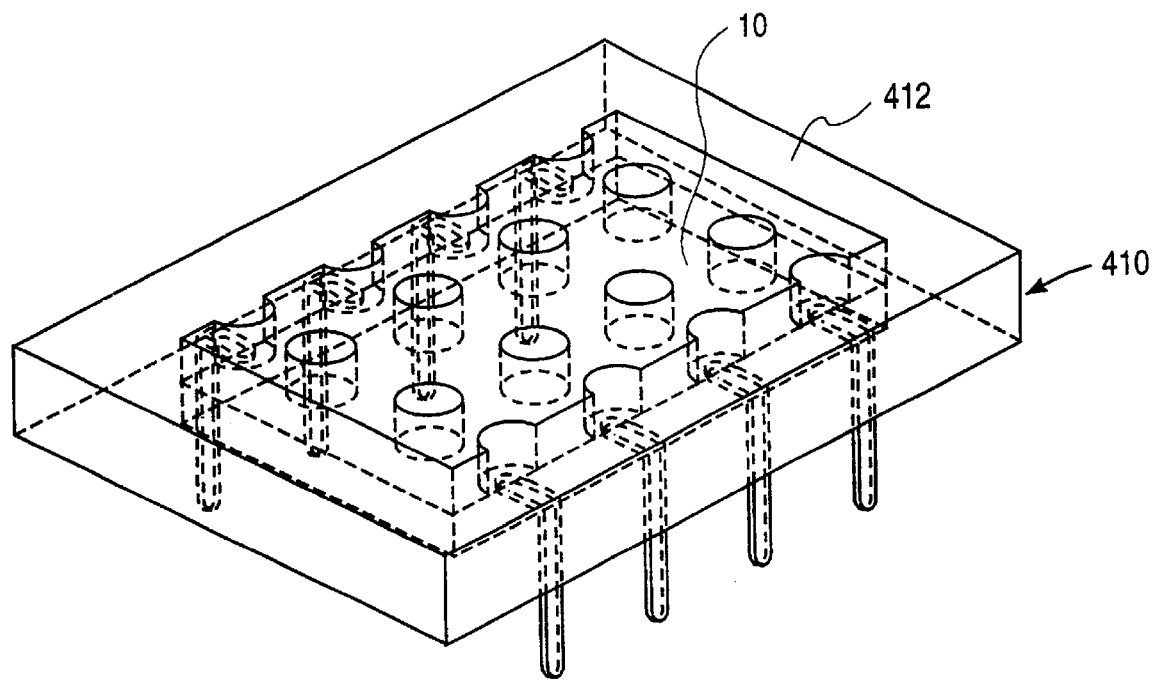
Figure 4D:
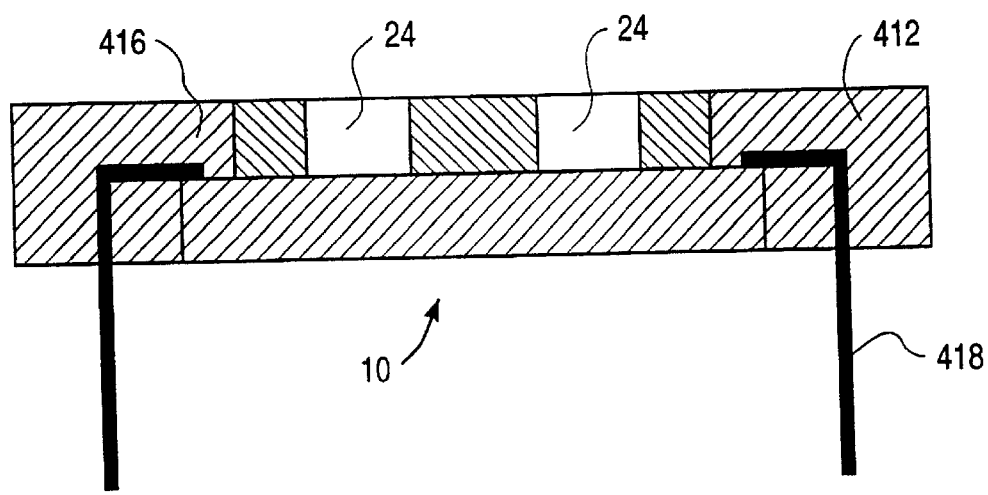

In an alternate aspect, the device shown in FIG. 4A is inserted into a complementary coupler assembly which contains the electrical leads from the controller, or appropriate interface circuitry for interfacing each electrical contact pad on the device with one of the leads. Each lead or portion of interfacing circuitry, is appropriately positioned within the coupler assembly to contact a separate electrical contact pad on one edge of the device. This alternate construction is illustrated in FIGS. 4B, 4C and 4D. In particular, FIG. 4B shows the microfluidic device 10 and the coupler assembly 410. The coupler assembly includes a main body portion 412 which has an opening 414 disposed through it, which opening is adapted to receive the device 10. As shown, this opening includes protruding portions 416 along the inner edge of the opening, which extend into the opening and are positioned and shaped to mate with the recessed regions 402 on the device 10. Electrical circuitry, in the form of an electrical interface pin 418, is mounted on the bottom surface of each of these protruding portions of the adapter whereby the electrical interface pin will contact the electrical contact pad disposed on the exposed surface 404 within the recessed regions 402 of the device. Each electrical interface pin extends out from the coupler assembly so as to provide a connection point at which the pin may be coupled to an appropriate electrical lead from the controller. As shown in FIGS. 4B–4D, each pin 418 is angled, e.g., at a 90° angle, so that it contacts the contact pad in a recessed region on the device in a horizontal orientation, but extends out the bottom surface of the coupler assembly 410 in a vertical orientation, past the device 10. Further, each electrical interface pin is also recessed, or disposed within a slot, on the bottom surface of the protruding portion and interior edge of the opening in the coupler assembly's body structure. This permits a snug fit between the device and the coupler assembly.

The overall device/coupler assembly is particularly advantageous in providing a microfluidic system that is readily interfaced with an electrical controller, simply by plugging the overall device/coupler into an appropriately configured electrical connection. In some aspects, the orientation of the electrical interface pins extending from the bottom of the device/coupler assembly, is the same as that orientation used in conventional integrated circuits, e.g., dual in-line orientation, thereby providing ready access to commercial sources for many of the interfacing components.

FIGS. 4C and 4D illustrate perspective and end views of the microfluidic device/coupler assembly in its assembled form. FIG. 4D illustrates the mating of the device 10 with the coupler assembly 410, from an end view, showing the contact between the electrical interface pins 418 and the contact pads on the exposed surface 404 in the recessed regions of the device. Although shown as a removable part, the coupler assembly is optionally provided attached to the microfluidic device, e.g., via an adhesive, or acoustically welded.

In addition to providing simple interfacing between the microfluidic device and the electrical controller, the electrical interface array shown in the device of FIGS. 4A–4D also provides advantages in terms of ease of manufacturing. In particular, preferred methods of fabricating microfluidic devices, as described above, are readily adapted to the fabrication of devices employing these structures. In particular, as noted previously, the microfluidic devices of the present invention are preferably manufactured from larger substrate wafers or plates which are bonded together to form an aggregate plate or wafer containing a number of devices as a single unit, produced in a single process. These devices are then separated from the larger wafer or plate into individual devices.

Figure 5:
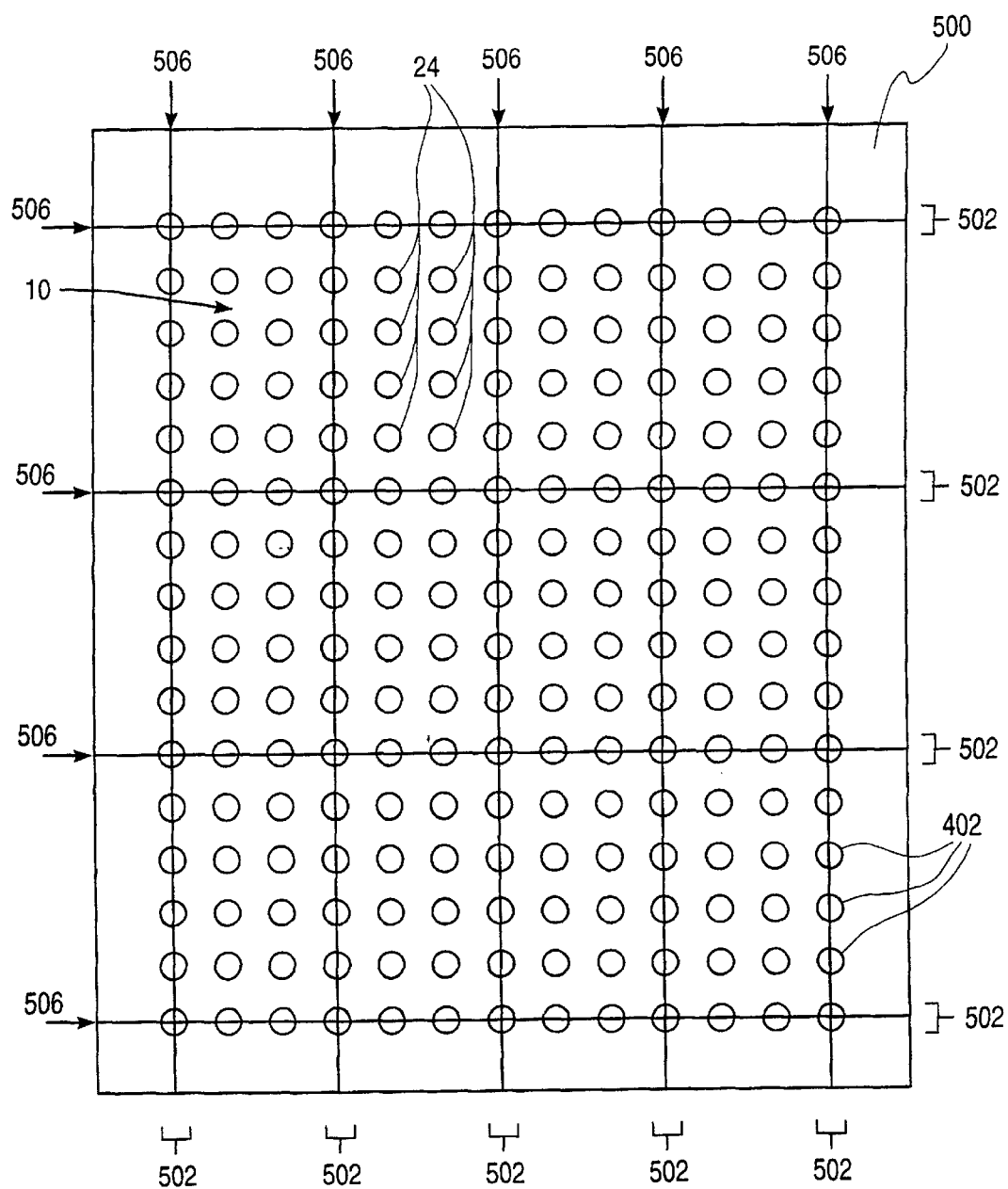
FIG. 5 illustrates a substrate wafer from which a number of microfluidic devices incorporating the electrical interface array shown in FIG. 4 are manufactured.

The recessed regions in the top substrate are provided by providing extra rows and columns of holes or ports in the top substrate wafer, between those holes or ports that are required to provide fluid access to the channels in the interior portion of the device. The individual devices are then separated from the larger aggregate wafer or plate, by scribing or sawing through the middle of the holes or ports that are within these extra rows and columns. This is illustrated in FIG. 5, which shows a substrate wafer or plate 500 from which several individual devices 10 are produced. The top substrate wafer or plate 500 includes the various ports 24 required for fluid access to the channels and chambers of each individual device. However, The substrate wafer or plate also includes additional rows and columns of ports 502, which serve to form the recessed regions of the top substrate in each device. Cut or scribe lines 506 illustrate the pattern of separating the individual devices from the lager wafer or plate, whereby each device will be provided with these recessed regions along each edge of each device.

In addition to providing substantially more user friendly systems, the improved interfaces described herein also provide a number of additional advantages. In one example, the devices incorporating these improved interfaces are fabricated as multi-device units, e.g., a single body structure incorporating two discrete and separate channel networks or microfluidic systems therein. In such cases, each separate system, e.g., each channel network, includes a separate interface array as described above. These interface arrays may be coupled with corresponding control elements for simultaneous or tandem operation, or optionally, can be rotated within a single control unit for successive operation.

In this latter mode, the microfluidic device includes a first interface component on the body structure capable of delivering energy to the first channel network, and a second interface component on the body structure capable of delivering energy to the second channel network. Although the instant invention is generally described in terms of transmission of electrical energy to each of the channel networks from a controller unit, interface arrays for transmission of other types of energy are also contemplated. For example, interface arrays for transmission of heat energy, light or other electromagnetic radiation, pressure, and the like, are optionally incorporated into the systems described herein.

As noted above, the overall system described herein, also includes a controller unit which includes an energy source such as an electrical power supply as described above, although, again, light sources, heat sources, pressure sources and the like are also contemplated. The controller includes a first surface adapted for mounting the body structure of the microfluidic device thereon. Typically, this surface includes appropriate structural elements, e.g., alignment pins, holes, grooves, slots, tabs, walls or the like, which are complementary and correspond to like structures on the body of the device, such that the body structure of the device mounted on the surface is maintained in one of at least two fixed orientations, and preferably, at least four different orientations. The surface region of the controller also includes at least a third interface component which is operably coupled to the energy source, e.g., via electrical circuitry, optical trains, pressure conduits and the like. This third interface component is typically oriented on the controller surface such that it is in communication with the first interface component on the body structure when the device is mounted in one orientation, and in communication with the second interface component on the body structure of the device when the device is mounted on the controller in the second orientation. When the interface component on the controller is in communication with the interface components on the body structure, it is capable of transmitting the energy from the energy source to those interface components and their respective channel networks.

In the case of the use of electrical energy, e.g., in controlling and directing electrokinetic flow within each of the channel networks of the device, the interface components present on the device's body structure and on the controller typically incorporate any of the previously described electrical interface structures. For example, the interface component on the controller typically includes multi-port electrical couplers, electrode pin arrays, and the like, while the interface component present on the device is the complementary structure, e.g., the electrical contact pads, or port/reservoir arrays described above.

In the case of the use of light energy, the interface array on the body structure of the device typically comprises an optically transparent window which is capable of transmitting the light energy to or from one or more of the channels in each separate channel network. The interface component on the controller typically includes appropriate optics for directing the light energy from the light source in the controller unit to the window.

Although described in terms of the transmission of energy from the controller to the channel networks of the device via the interface component on the controller, through the interface component on the body of the device, the present invention also envisions the flow of energy in the opposite direction, i.e., the transmission of energy from the respective channel networks through the interface components on the body structure, and the receipt of this energy by the interface component on the controller. In this mode of operation, the controller typically includes energy detection systems for detecting energy, e.g., signals, originating from the respective channel networks. Examples of such energy or signals include optical signals, such as fluorescent, chemiluminescent or calorimetric signals, thermal signals, or electrical signals, such as in the determination of resistances or voltages within the channel networks, or other potentiometric or amperometric signals relating to the chemical environment within the channels.

Figure 6:
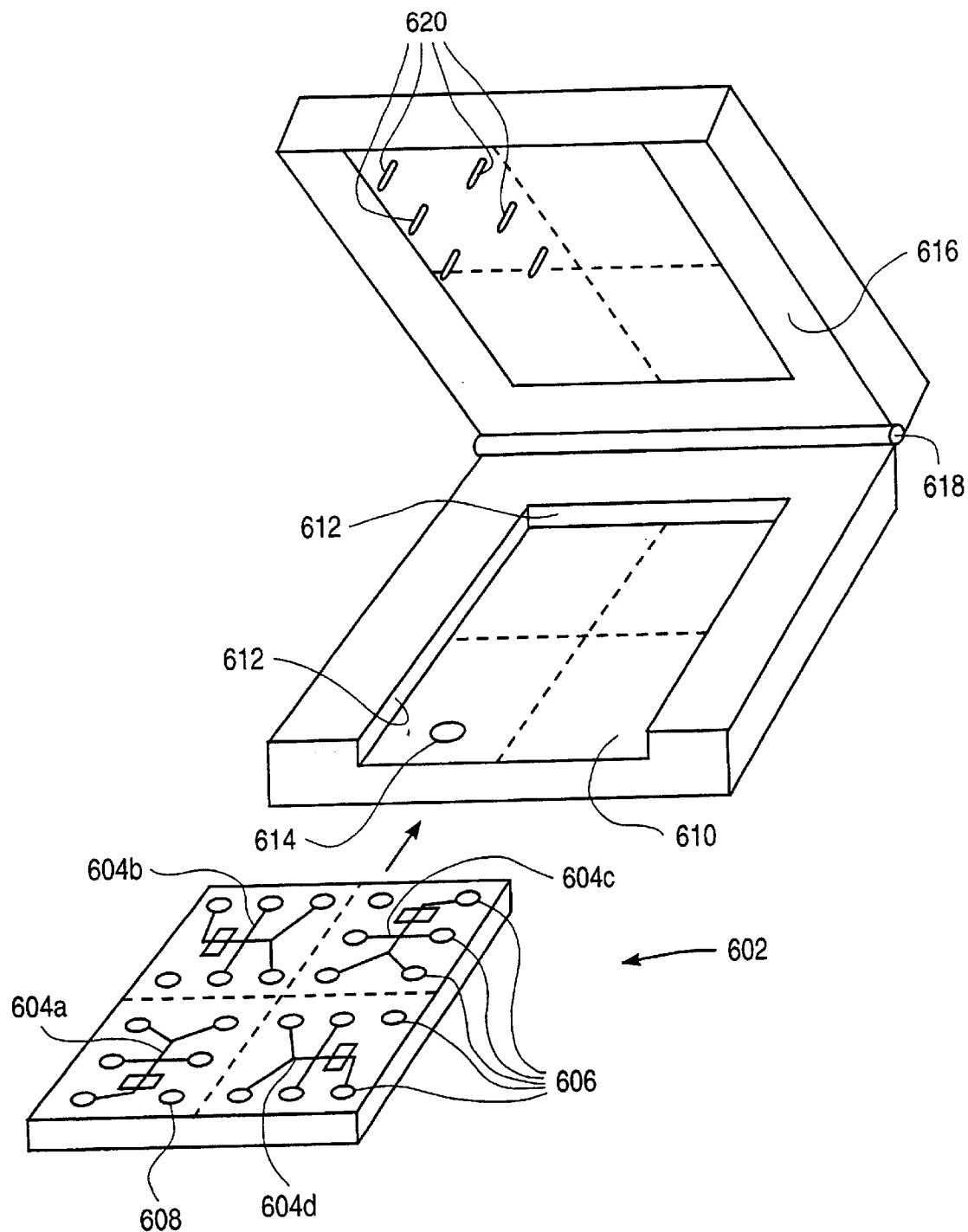
FIG. 6 illustrates a microfluidic system incorporating interface elements on the device and controller which are in communication when the device is inserted into the controller in any of a number of fixed or predetermined orientations.

An illustration of an embodiment of the interchanging interfacing systems described herein is shown in FIG. 6. As shown, the body structure 602 of the device includes within its interior portion, four separate channel networks 604a, 604b, 604c and 604d. Each of the four separate channel networks includes a first interface component in the form of a plurality of ports 606 in fluid communication with that channel network. Each channel network also includes an optical detection window 608 disposed over one of the channels in each of the channel networks. The controller includes a mounting surface 610 which includes retaining walls 612 for maintaining the body structure in one of four fixed orientations when it is inserted into the controller. The mounting surface includes a first interface component in the form of optical detector 614, which is oriented on the mounting surface 610 such that it is disposed adjacent to the optical detection window on one of channel networks 604a–d, e.g., 604a when the device is inserted into the controller in the orientation shown. As shown the controller also includes a cover element 616 coupled to the mounting surface via hinge 618. The cover element 616 includes an additional interface component in the form of an array of electrode pins 620, which electrode pins are electrically coupled to an electrical controller, e.g., as described above. The electrode array is oriented on the cover such that when the cover element is closed over the body structure inserted into the controller, the electrode pins are inserted into the ports of one of the channel networks, e.g., into channel network 604a in the orientation shown.

Inserting the body structure into the controller in a first orientation presents the interface components of one channel network to the interface components of the controller. Rotation of the body structure 602 in the horizontal plane, e.g., 90 degrees, then presents the interface components of a second channel network 604b to the interface components of the controller. This type of rotatable structure permits one to load fluids, samples and the like into a number of separate device/channel networks, which are then subject to successive analysis etc., simply by rotating the body structure and reinserting it into the controller. This greatly reduces the amount of time required to perform a large number of particular analyses or other fluidic manipulations on samples and the like.

Figure 7:
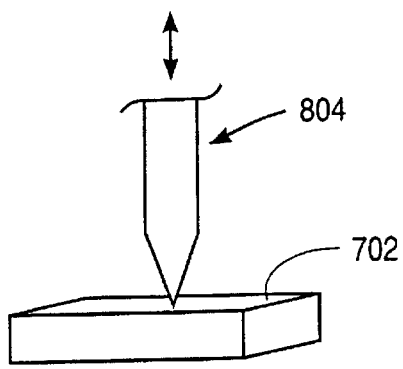
FIG. 7 schematically illustrates an electrical coupling arrangement in which a substantially rigid electrode pin mates with a thin, flat electrode surface.

Referring now to FIG. 7, it will often be advantageous to provide electrical coupling between the interface system and the microfluidic channels without directly contacting sample fluids with an electrode of the interface system. For example, when a first microfluidic device is to be removed from its clamshell interface structure and replaced with an alternate microfluidic device with different fluids, the use of electrodes which extend first into the fluids of the first device, and then into the fluids of the second device poses a risk of cross-contamination. Additionally, as the fluid samples may include corrosive agents, there is some risk of electrode degradation over time.

To avoid cross-contamination and degradation of the interface electrical components when using corrosive fluids, the microfluidic devices of the present invention may include thin, flat electrodes or pads 702 which are electrically coupled to the fluids within the channel system, but which extend outside the channel system so that at least a portion of the flat electrode surface is not in fluid continuity with the intersecting channels. Electrical coupling between the clamshell interface structure and the thin, flat electrode may optionally be provided by simply having an electrode pin of the clamshell cover extend down so as to be in direct contact with the flat electrode of the microfluidic device when the cover is in the closed position, as shown in FIG. 7.

Unfortunately, direct contact electrical coupling between a thin, flat electrode on the microfluidic device and a pin extending from the clamshell cover can have significant disadvantages. Specifically, the pin electrodes may be substantially rigid structures. If such a rigid pin electrode extends too far from the cover, the pin will advance beyond the initial point of contact. As the distal tip of pin electrode 804 advances against a thin, film electrode 702, large stresses can be generated. These stress can cause failure of the electrical contact due to fracture of the flat electrode 702, breakage of the pin electrode 804, or piercing of a surface coating, electrode film, bonding layer, or the underlying microfluidic device body structure. However, if rigid pin 704 does not advance far enough to provide contact between the pin and the flat electrode 702, the electrical coupling between these structures will be unreliable. Hence, it would be beneficial to provide alternative coupling arrangements which offered greater reliability, without excessively tight tolerances, complex contact biasing mechanisms, or the like.

Figure 8:
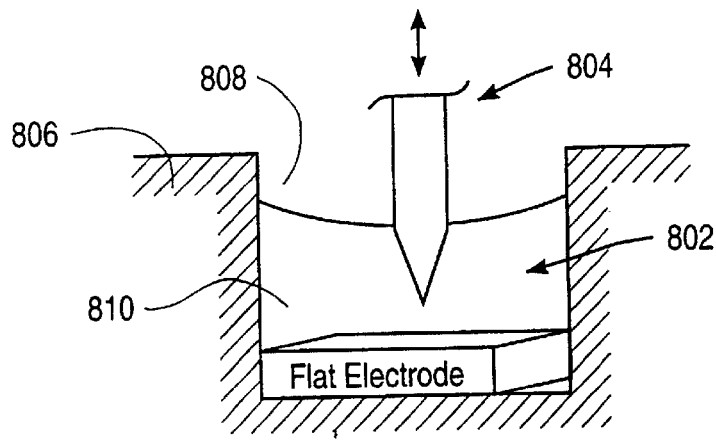
FIG. 8 schematically illustrates an alternative coupling arrangement in which a substantially rigid electrode pin is electrically coupled to a thin, flat electrode using an electrolyte to avoid damage to the flat electrode during coupling.

As illustrated in FIG. 8, in order to provide reliable and compliant electrical coupling of a thin film, flat electrode 802 with a rigid pin electrode 804, a microfluidic device body 806 includes a fluidically isolated port 808 containing an electrolyte solution 810. When pin electrode 804 extends into electrolyte 810, the electrolyte can provide complaint electrical coupling between the thin, flat electrode 802 and pin without damage to either. This provides a highly efficient electrical coupling with relatively loose tolerances, as pin electrode 804 need not even be in contact with the thin (and sometime mechanically delicate) flat electrode 802.

Pin 804 will often comprise a conductive metal, typically comprising, e.g., platinum, gold, titanium, or the like, and ideally comprising platinum. Pin electrode 804 will generally be rigidly affixed to the rotatable cover of a clam shell interface system as described above, but may alternatively be mechanically coupled to the microfluidic device support base by a wide variety of detachable, sliding, pivoting, and/or linear joints so as to maintain alignment between the pin electrode and port 808. Pin 804 will generally have a length in the range from about to 2 mm to about 10 mm inches, and a diameter from about 50 m$\mu$ to about 2 mm. Other dimensions, outside these ranges, may also be useful in certain situations.

Thin, flat electrode 802 may be fabricated from an appropriately conductive material, and will often be disposed at least in part between the layers of a multi-layer microfluidic device body structure. For example, thin, flat electrodes may be provided by depositing an appropriately conductive material upon an upper surface of a lower substrate layer prior to bonding the upper and lower substrate layers together. A variety of well known deposition methods might be employed, including chemical vapor deposition, sputtering, thermal or E beam evaporation, electroplating, and the like. The electrode and electrode coupling circuitry may again be defined with a photographic lift-off technique. As was also described above, port 808 may be formed by bonding the upper and lower substrate layers together after forming an opening through the upper layer. The upper and lower layers are aligned during bonding so as to electrically expose flat electrode 802 within the opening of port 808.

Thin flat electrode 802 may comprise any of the electrode and/or circuitry materials described above. Ideally, flat electrode 802 will comprise structures similar to the circuitry described above with reference to FIGS. 3A–C.

Electrolyte 810 is fluidically isolated from the sample fluids in the channel system by the structure of the microfluidic device. Hence, there is little or no danger of cross-contamination when pin electrode 804 is removed from port 808, the microfluidic device is removed and replaced by an alternative device having a different fluid sample to be tested, and pin 804 is advanced into the coupling port of that other device. Hence, electrolyte 810 may comprise a wide variety of alternative fluids. Electrolyte 810 will preferably be non-corrosive so as to allow long term use of pin electrode 804 with minimal degradation. Suitable electrolyte fluids may include saline, conductive buffer, KCl, NaCl, or the like.

Figure 9A:
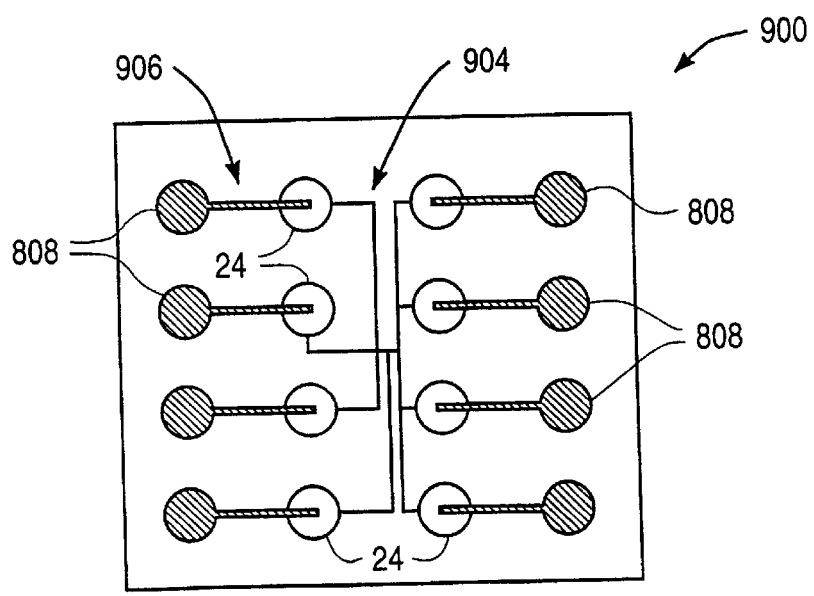
FIGS. 9A and B illustrate a microfluidic device having ports which are in electrical continuity with fluid sample ports, but which are not in fluid continuity with the sample ports so as to avoid-cross-contamination of samples when the microfluidic device is removed and replaced from the interface structure.
Figure 9B:
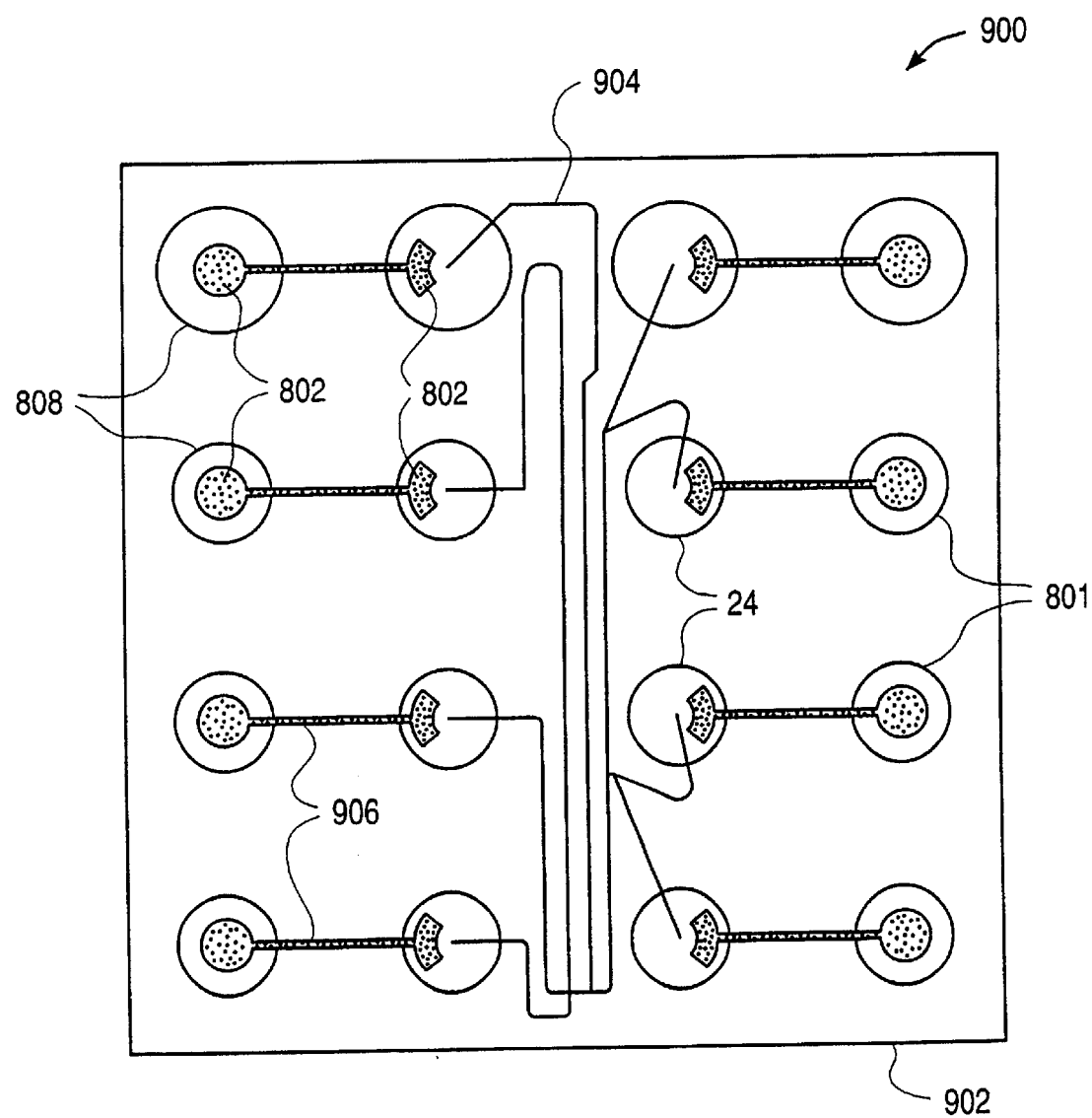

An exemplary microfluidic device including fluidically isolated electrical coupling ports is illustrated schematically in FIG. 9A, and in more detail in FIG. 9B. Microfluidic device 900 again has a substrate body 902 defining a plurality of intersecting microfluidic channels 904. Ports 24 are often disposed at unintersected termini of the channel system, and fluids within the channel system be transported electrokinetically by applying voltages to the fluids within these ports, as described above.

To provide electrical coupling with the fluid in ports 24, fluidicly isolated ports 808 are in electrical continuity with ports 24, but are not in fluid continuity with the channel system. To provide this electrically continuity, thin, flat electrodes 802 extend between fluidically isolated ports 808 and ports 24. Hence, the electrode material defines an inter-port conductor 906. To efficiently electrically couple the fluids within the ports, flat electrodes 802 will typically have a surface area of between about 100 $\mu m^2$ and 20 $mm^2$ within each of ports 808 and ports 24. Inter-port conductor 906 will typically have a width which is substantially greater than its thickness, the width typically allowing the conductor to withstand the normal current densities described above. As no fluid coupling is provided between isolated ports 808 and 24, inter-port conductors 906 are generally the only electrical coupling provided between the fluids contained therein.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A microfluidic device comprising:

a body structure including an upper layer and a bottom layer, the body structure having an interior portion defining first and second intersecting microscale channels, the first channel having an unintersected terminus, the upper layer having first and second ports therethrough, the first port disposed at the terminus of the first channel, the interior portion blocking fluid communication between the first port and the second port; and an electrically conductive film disposed between the lower and upper layers, the film electrically and physically, coupling a first fluid in the first port with a second fluid in the second port, the first fluid being different than the second fluid.

2. The device of claim 1, further comprising an electrode movable between a first position and a second position, the electrode in the first position being clear of the body structure, the electrode in the second position extending downward into the second port so that the second port electrically couples the electrode to the conductive film.

3. The device of claim 2, wherein the second port defines an axis, wherein the conductive film extends along a plane at an angle to the port axis, wherein the electrode moves axially between the first position and the second position, and wherein the electrode in the second position is separated from the film so as to avoid damaging the film when the electrode moves.

* * * * *